US005474930A

United States Patent [19]

Barnes

[11] Patent Number: 5,474,930
[45] Date of Patent: Dec. 12, 1995

[54] NON-TUMORIGENIC CELL LINES FOR EXPRESSION OF GENES

[75] Inventor: David W. Barnes, Corvallis, Oreg.

[73] Assignee: The State of Oregon, Eugene, Oreg.

[21] Appl. No.: 177,637

[22] Filed: Jan. 4, 1994

Related U.S. Application Data

[63] Continuation of Ser. No. 852,490, Mar. 16, 1992, abandoned, which is a continuation of Ser. No. 540,460, Jun. 18, 1990, abandoned, which is a continuation of Ser. No. 35,814, Apr. 18, 1987, abandoned.

[51] Int. Cl.$^6$ .............................. C12N 5/00; C12N 15/00
[52] U.S. Cl. ........................ 435/240.2; 435/172.3; 435/69.1; 935/70
[58] Field of Search ............................. 435/69.1, 172.3, 435/240.2; 935/70

[56] References Cited

U.S. PATENT DOCUMENTS 4,757,006  7/1988  Toole et al. ............................... 435/70
4,766,075  8/1988  Goeddel et al. ...................... 435/240.2

OTHER PUBLICATIONS

Shipley et al., In Vitro 17: 656–670 (1981).
Serrero et al., Cell Prolif. 6: 523–530 (1979).
Scahill et al., Proc. Natl. Acad. Sci. 80: 4654–4658 (1983).
Ciguere et al., J. Cell. Physiol. 110: 72–80 (1982).
Brandi et al., Proc. Natl. Acad. Sci. 83: 1709–1713 (1986).
Barnes et al., (a), Cell 22: 649–655 (1980).
Barnes et al. (b), Analytical Bioch. 102: 255–270 (1980).
Hammond et al., Proc. Natl. Acad. Sci. 81: 5435–5439. (1984).
Thomassen et al., Concinogenesis 7: 2033–2039 (1986).
F. S. Ambesi–Impiombato et al., "Culture of Hormone–Dependent Functional Epithelial Cells from Rat Thyroids," *Proc. natl. Acad. Sci. USA* 77:3455–3459, 1980.
Vincent J. Cristofalo et al., "Cellular Senescence In Vitro," *Advances in Cell Structure* 2: 1–68, 1982.

Primary Examiner—Jasemine C. Chambers
Attorney, Agent, or Firm—Seed and Berry

[57] ABSTRACT

Non-tumorigenic cell lines capable of indefinite growth in serum-free media are disclosed. The cell lines are capable of expressing exogenously introduced genes, and may be derived from mouse embryo cells. Methods for producing proteins utilizing these cell lines, and methods for selectively controlling the growth of the cell lines are also disclosed.

9 Claims, 2 Drawing Sheets

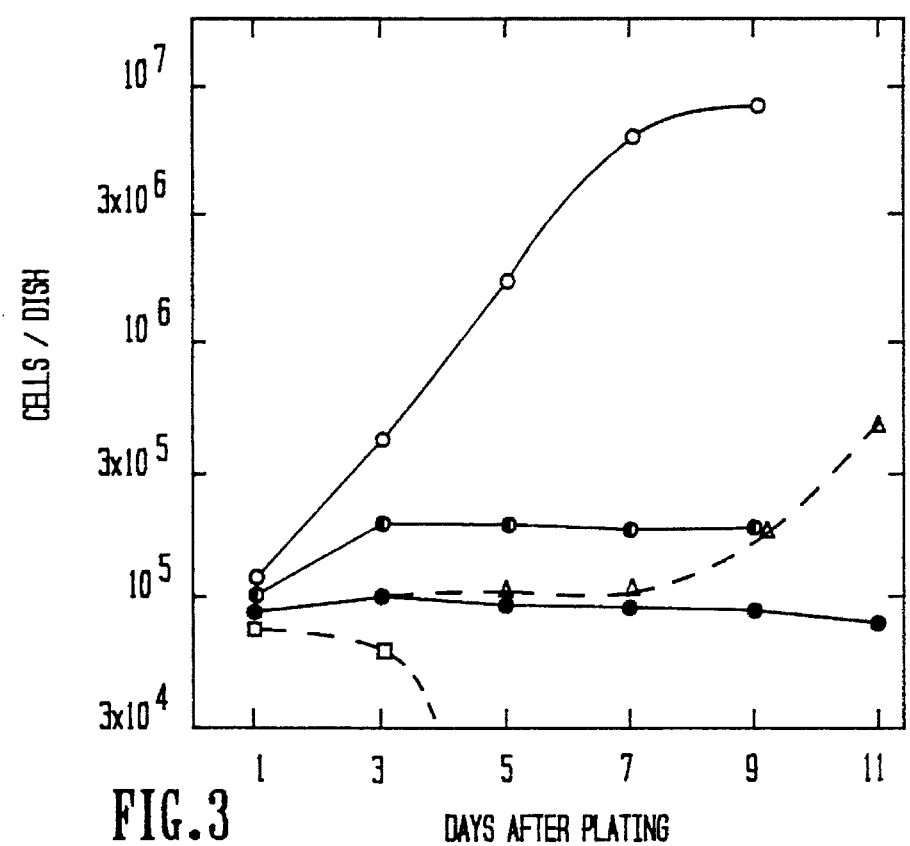
FIG.3  DAYS AFTER PLATING
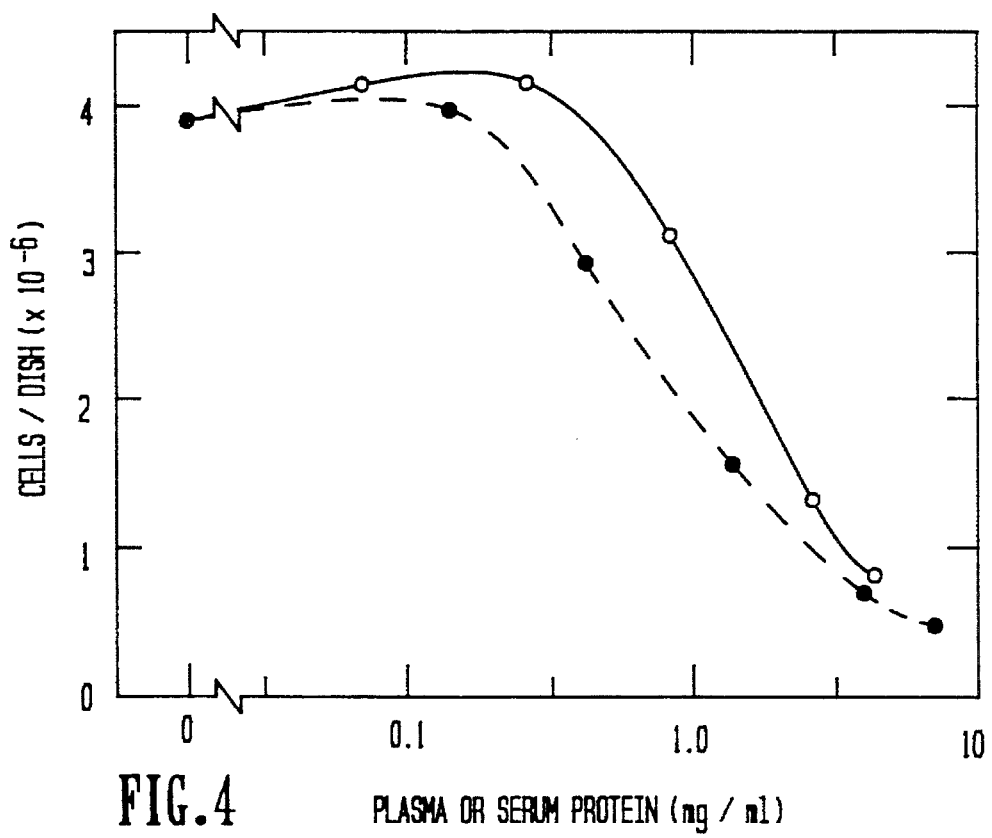
FIG.4  PLASMA OR SERUM PROTEIN (mg/ml)

NON-TUMORIGENIC CELL LINES FOR EXPRESSION OF GENES

CROSS-REFERENCE TO RELATED APPLICATION

This application is a continuation of U.S. patent application Ser. No. 07/852,490, filed Mar. 16, 1992, now abandoned; which application was a continuation of U.S. patent application Ser. No. 07/540,460, filed Jun. 18, 1990, now abandoned; which application was a continuation of U.S. patent application Ser. No. 07/035,814, filed Apr. 8, 1987, now abandoned.

TECHNICAL FIELD

The present invention relates generally to cell lines capable of expressing selected genes of interest, and more particularly, to cell lines that can be propagated indefinitely under serum-free conditions, can be reversibly growth-inhibited, and are capable of expressing exogenously introduced genes.

BACKGROUND ART

There have been numerous attempts to express selected genes of interest using a variety of different cell lines. Conventional established mammalian cell lines, for instance, have been widely utilized in light of their capacity to grow quickly to high cell densities and in suspension, both desirable characteristics for the production of biological products. Examples of commonly used cell lines in this regard include the BHK, CHO, and COS cell lines. Often however, the growth of established cell lines such as these cannot be sufficiently controlled. This is a significant disadvantage in situations in which a high cell density has been achieved, and the primary purpose becomes collection of the biological product rather than generation of increasing cell numbers. In addition, established cell lines almost without exception exhibit an abnormal karyotype. These cell lines are often either tumorigenic in vivo, or give rise to tumorigenic cells upon further proliferation and extended culture. Tumorigenicity is a significant concern when selecting a cell line from which biological products will be isolated.

An additional disadvantage of conventional established cell lines is that they are isolated and propagated in culture media containing a serum supplement. Further, these cell lines often require a serum supplement for continued growth (Barnes and Sato, Cell 22:649–655, 1980). This requirement for serum creates a source of additional expense, problems relating to quality control and reproducibility of the serum, and problems in isolating desired biological substances.

In contrast to established cell lines, normal cell lines in early passages exhibit a predominantly diploid karyotype and are non-tumorigenic. However, these cells, known as primary cells, characteristically undergo alterations upon multiple passages. Consequently, the culture eventually degenerates or undergoes multiple genetic and phenotypic changes, often resulting in the development of tumorigenic cells, making further passage of primary cells undesirable for the production of biological products.

While there have been attempts to utilize serum-free media to generate cell lines capable of continuous growth without subsequent degeneration or chromosomal aberration, these efforts have been only partially successful. Consequently, there is a need in the art for a cell line capable of indefinite growth under serum-free conditions, the cell line further being capable of expressing exogenously introduced genes. In addition, the cell line should be capable of growth to high density in suspension, the growth of the cell line also being subject to selective control. The present invention fulfills this need and further provides other related advantages.

DISCLOSURE OF THE INVENTION

Briefly stated, the present invention discloses a non-tumorigenic cell lines capable of indefinite growth in serum-free media, the cell lines being further capable expressing exogenously introduced genes. In one particular embodiment, the cell line is derived from mouse embryo cells. (Hereinafter referred to as "serum free mouse embryo" or "SFME").

Another aspect of the present invention discloses a method for producing a desired protein. The method generally comprises (a) introducing a gene encoding the desired protein into a non-tumorigenic cell line capable of indefinite growth in serum-free media; (b) growing the cell line in a serum-free medium; and (c) isolating the protein product encoded by the gene and produced by the cell line.

Yet another aspect of the present invention discloses a method for selectively controlling the growth of a non-tumorigenic cell line capable of indefinite growth in serum-free media. The method generally comprises growing the cell line in serum-free media and subsequently supplementing the media, either briefly or continually, with an effective amount of a selected biological substance. Suitable biological substances in this regard include serum, plasma, conditioned cell culture medium, tissue extracts, or purified or partially purified components thereof, peptide growth factors, glycocorticoids, thyroid hormones, retinoids or other hormonal or related compounds.

Other aspects of the invention will become evident upon reference to the following detailed description and attached drawings.

BRIEF DESCRIPTION OF THE DRAWINGS

FIG. 3 shows the inhibitory effect of serum upon the growth of SFME cells. ○, serum-free culture medium, as described in Example I, infra; ●, culture medium containing 10% calf serum; ), ◐, serum-free culture medium containing 10% calf serum; ☐, serum-free culture medium lacking epidermal growth factor (EGF); △, 3-days growth in culture medium containing 10% calf serum, followed by culture in serum-free medium.

FIG. 4 illustrates growth inhibition of SFME cells in serum-free medium containing various concentrations of plasma or serum. ●, calf serum; ○, plasma.

BEST MODE FOR CARRYING OUT THE INVENTION

Figure 2:
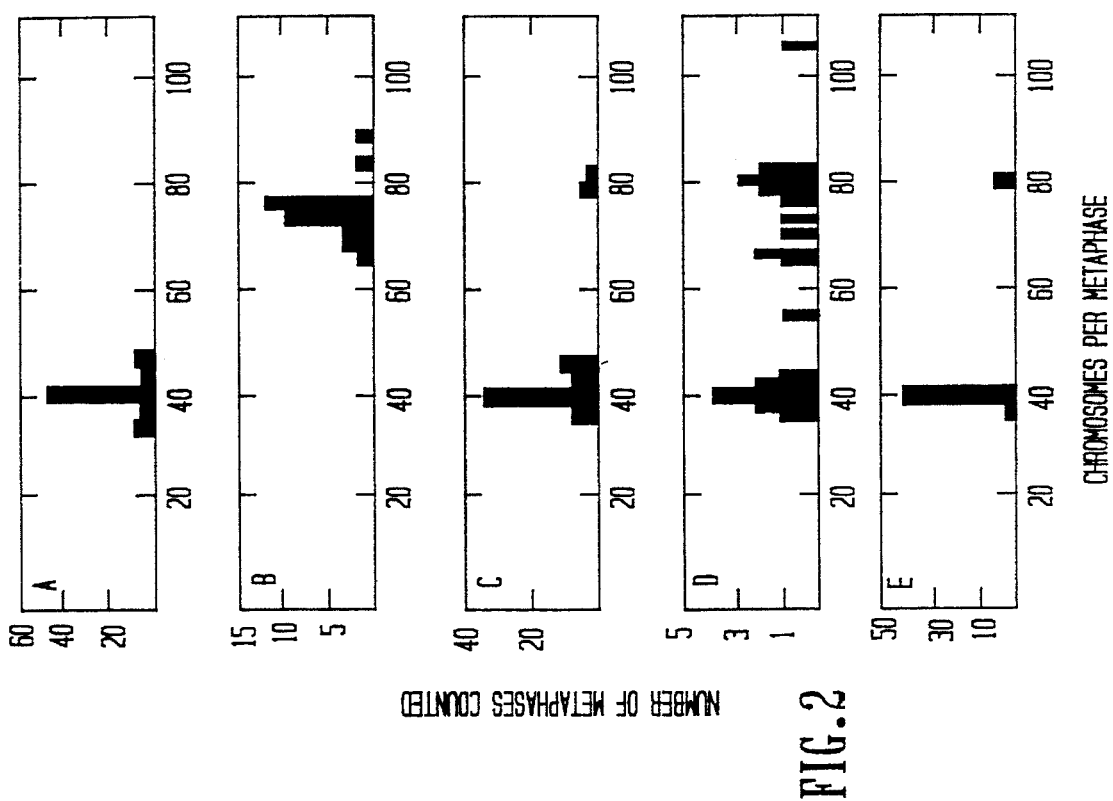
FIG. 2 depicts karyotyping data obtained with Swiss mouse and BALB/c mouse embryo cell lines grown in serum-containing and serum-free culture medium. (A) primary Swiss mouse embryo cells cultured in medium containing 10% calf serum (2 population doublings); (B) post-crisis Swiss mouse embryo cells cultured in medium containing 10% calf serum (20 population doublings); (C) SFME cells cultured in serum-free medium (200 population doublings); (D) BALB/c mouse embryo cells cultured in medium containing 10% calf serum (7 population doublings); (E) BALB/c SFME cells cultured in serum-free medium (70 population doublings).

Prior to setting forth the invention, it may be helpful to an understanding thereof to set forth definitions of certain terms to be used hereinafter.

Serum-free media: Tissue culture media in which the mammalian blood product supplement, usually serum, is replaced with a defined supplement. The defined supplement contains discrete amounts of known components that, in combination, support the growth of cultured animal cells. A typical serum-free medium formulation may include nutrients, buffers, hormones, salts, antibiotics, proteins, growth factors, and enzymes.

Indefinite growth: A property of some cultured cells, especially established cell lines, that permits extended propagation of one lineage of cells. This characteristic is in contrast to that exhibited by most normal diploid cells isolated and cultivated in vitro, which undergo senescence upon multiple passages. Within the present invention, indefinite growth includes culture for more than thirty generations.

As described herein, Swiss SFME cells have been cultured for 200 generations with no evidence of senescence, and BALB/c SFME cells have been cultured for 150 generations without senescence. As compared to Swiss or BALB/c embryo cultures maintained under conventional, serum-containing conditions, the SFME cell lines have been grown for ten-fold or greater the number of generations, with no evidence of a decrease in growth rate.

Non-tumorigenic: Substances or cells that do not give rise to tumors when injected in vivo. Tumorigenicity is generally a correlate of phenotypic or genotypic changes that result in uncontrolled growth of abnormal cells. Within the present invention nontumorigenic cells are those cultures which can be injected subcutaneously into syngeneic or athymic mice at $10^7$ per mouse with no evidence of a decrease in growth rate.

As noted above, the present invention discloses non-tumorigenic cell lines capable of indefinite growth in serum-free medium. An additional advantage of such cell lines, as compared to the cell lines described in the prior art, is that the growth of the cell lines of the present invention can be controlled. Through control of growth, it is possible to substantially inhibit increases in the cellular biomass, while optimizing production of the expressed biological product. A further advantage of the disclosed cell lines is that purification of the desired biological product from a non-tumorigenic cell eliminates the risk of co-purification of tumorigenic materials.

The present invention also allows the extended in vitro growth in serum-free medium of non-tumorigenic cells capable of expressing foreign genes. A variety of mammals and tissues may be used for the derivation of cell lines suitable for use herein. Preferred cells in this regard are derived from mouse embryos and exhibit a predominately diploid karyotype. Particularly preferred cells are derived from embryos obtained from Swiss and BALB/c mice. It will be evident to one skilled in the art that embryonic and non-embryonic tissue derived from a variety of mouse species, as well as other warm-blooded species, including human, may be utilized within the present invention.

The non-tumorigenic cells of the present invention may be used to produce and recover biological products encoded by exogenously introduced foreign genes. Preferred genes include those encoding tissue plasminogen activator, factor VIII, interleukin II, insulin, growth hormone, tumor necrosis factors, antibodies, superoxide dismutase and other enzymes, peptide hormones and hormone receptors, and interferons. However, it will be evident to one skilled in the art that a variety of other foreign genes could be expressed by the disclosed non-tumorigenic cells. These foreign genes need only be properly introduced into the non-tumorigenic cell line in an appropriate configuration and orientation to obtain production and recovery of desired biological products. The cell lines disclosed within the present invention may also be utilized in conjunction with a selection system using dominant markers (for instance, neomycin resistance). In addition, the non-tumorigenic cell lines may be suitable host cells for an amplification system for introduced foreign genes.

As noted above, the non-tumorigenic cell lines described herein are capable of indefinite growth in serum-free medium. In a preferred embodiment, the cells may be grown in culture medium containing a defined supplement. A preferred defined supplement includes insulin, transferrin, epidermal growth factor (EGF), high-density lipoprocein (HDL), and fibronectin. It will be evident to one skilled in the art that this particular supplement is merely exemplary of those that may be utilized within the present invention. For instance, some components may be substituted for others (e.g., insulin-like growth factors for insulin; transforming growth factor alpha for epidermal growth factor; bovine serum albumin containing lipid for high-density lipoprotein; polylysine for fibronectin; and iron salts for transferin). Further, other factors might be added to the culture medium, such as tumor promoters, additional hormones and/or growth factors, bovine serum albumin, low concentrations of serum or plasma, or modified plasma preparations with reduced inhibitory activity. Fibronectin might be eliminated from the culture medium formulation to obtain anchorage-independent growth of the present cell lines. Alteration of culture medium components may also allow derivation of sublines of the non-tumorigenic cell lines of the present invention or their equivalent. In addition, other supplements may be added to the medium formulation to enhance protein production from a particular foreign gene construct (for example, addition of steroid hormones where the foreign gene is operably linked to a steroid hormone-responsive promoter).

A method for producing a foreign gene product utilizing the cell lines of the present invention is also disclosed. In a preferred embodiment, foreign genes are introduced by transfection into the non-tumorigenic cells described herein. In this regard, dextran sulfate-, calcium phosphate-, and electrophoration-mediated transfection are preferred, with calcium phosphate-mediated transfection particularly preferred. The foreign gene product is expressed by the non-tumorigenic cells, and the biological product can then be purified by a variety of techniques well known in the literature. These techniques include immuno-affinity chromatography, high-performance liquid chromatography, ion-exchange chromatography, precipitation techniques, hydrophobic or salt interaction techniques, isoelectric focusing, and electrophoresis techniques. In addition, similar techniques may be applied to the isolation of the foreign gene product from the culture medium in which the cells are grown or from the cells themselves.

A method for selectively controlling the growth of non-tumorigenic cell lines capable of indefinite growth in serum-free medium is also described within the present invention. In a preferred embodiment, growth is controlled by supplementing the non-tumorigenic cell culture medium with a selected amount of a synthetic or purified biological substance. Particularly preferred biological substances are serum, plasma, conditioned cell culture medium, tissue extracts, and purified or partially purified components thereof. However, it will be evident to one skilled in the art that a variety of blood products may be utilized within this methodology. Such blood products may include plasma products, such as Cohn fractions, or other blood product preparations isolated by chromatographic, precipitation, affinity, or electrophoretic techniques. Hormones, steroid hormones, peptide hormones, nutritional components, and vitamins or related compounds, such as retinoids, present in the blood may be used, either as free components or bound to carrier molecules. These free or bound preparations may then be added to the non-tumorigenic cell culture medium in an amount sufficient to control the growth of the cell line.

One advantageous use of the system described herein would be in the introduction of a gene under the influence of a hormone-responsive control element (e.g., the glucocorticoid responsive MMTV promoter) that responds to a hormone that inhibits SFME cell growth. Treatment of cells with such a hormone would simultaneously inhibit all growth and stimulate protein synthesis.

To summarize the examples which follow, Example I describes a serum-free medium useful for the isolation and propagation of a non-tumorigenic cell line. The derivation of the SFME mouse embryo cell lines in this serum-free medium is also disclosed. Example II illustrates that the cells which are isolated and maintained in serum-free medium exhibit a predominately diploid karyotype, while cell lines which are isolated in serum-containing medium display an abnormal tetraploid karyotype. Example III illustrates that Swiss SFME mouse embryo cells, which were cultured for over 200 generations in serum-free medium, were non-tumorigenic upon injection of the cells subcutaneously into 4- and 7-week-old male and female athymic Swiss mice. The mice were observed for six months, and no evidence of any tumorigenic activity was observed. However, oncogene-transformed SFME cells did show tumorigenic qualities after injections into athymic Swiss mice. Example IV sets forth an analysis of the effects of individual defined supplement components in the growth of SFME cells in vitro. Example V presents a study of the inhibitory effects of the addition of serum to cells isolated and grown in serum-free medium. Example VI describes the transfection of the SFME cell line with the Ha-ras gene.

The following examples are offered by way of illustration, and not by way of limitation.

EXAMPLES

EXAMPLE I

Serum-Free Medium for the Preparation and Maintenance of Mouse Embryo Cell Cultures The serum-free medium used was a one-to-one mixture of Ham's F12 and Dulbecco-modified Eagle's medium containing 4.5 g/l glucose (F12:DME) supplemented with bovine insulin (10 ug/ml; Sigma Chemical Co., St. Louis, Mo.), human transferrin (25 ug/ml; Sigma), human high-density lipoprotein (HDL; 20 ug/ml; Meloy Laboratories, Springfield, Va.), mouse epidermal growth actor (EGF; 50 ng/ml; Collaborative Research, Inc., Waltham, Mass.), human fibronectin (20 ug/ml; Meloy), sodium selenite (10 nM), human platelet-derived growth factor (PDGF; 1 unit/ml), penicillin (200 U/ml), streptomycin (200 ug/ml) ampicillin (25 ug/ml), 15 mM 4-(2-hydroxy-ethyl)-1-piperazine-ethanesulfonic acid (pH 7.4), and 1.2 g/ml sodium bicarbonate.

Sterile stock solutions of supplement components may be stored in the refrigerator, or may be stored in aliquots at −20° C. for longer periods of time. Water utilized for the preparation of concentrated stock solutions of supplement components and for the preparation of the medium is purified by passage through a Milli-Q (Millipore, Bedford, Mass.) water purification system immediately prior to use. F12:DME is prepared from powdered formulations (GIBCO, Grand Island, N.Y.), and may be stored frozen at −20° C. for a maximum period of three weeks. All solutions and medium formulations are stored in reusable plastic containers. Polypropylene tubes are used for concentrated stocks, and 250 ml polystyrene flasks are used for storing media. All pipets and culture vessels are disposable plastic (Falcon or Corning).

Insulin, transferrin, EGF and HDL are added to the F12:DME medium after plating of the cells, by means of addition of small aliquots from concentrated stocks. Insulin is prepared at 1 mg/ml in 20 mM HCl; transferrin is made at 5 mg/ml in phosphate-buffered saline. Both insulin and transferrin concentrated stocks are filter-sterilized after preparation. EGF, PDGF and fibronectin are obtained as sterile, lyophilized powders from commercial sources (e.g., Collaborative Research; Meloy). These lyophilized preparations are reconstituted with sterile water or sterile buffered salt solutions. HDL is obtained commercially (Meloy) as a sterile solution.

Fibronectin is provided to the cultured cells by precoating culture flasks for 30 minutes with 4 ml of a solution of fibronectin at 20 ug/ml in F12:DME, with removal of the precoating solution prior to plating the cells.

The SFME mouse embryo cell line was derived in serum-free medium by trypsinization of minced, pooled 16-day Swiss mouse embryos, followed by plating of the cells at a density of $3 \times 10^6$ cells/25 $cm^2$ tissue culture flask. Trypsinization was accomplished with 0.1% crude trypsin and 1 mM ethylenediaminetetraacetate (EDTA) in phosphate-buffered saline. The trypsinized cell suspension was then diluted into an equal volume of serum-free culture medium containing 0.1% soybean trypsin inhibitor prior to centrifugation of the cells and resuspension in fresh medium. The cells were then grown in a 5% $CO_2$-95% air atmosphere at 37° C.

Figure 1:
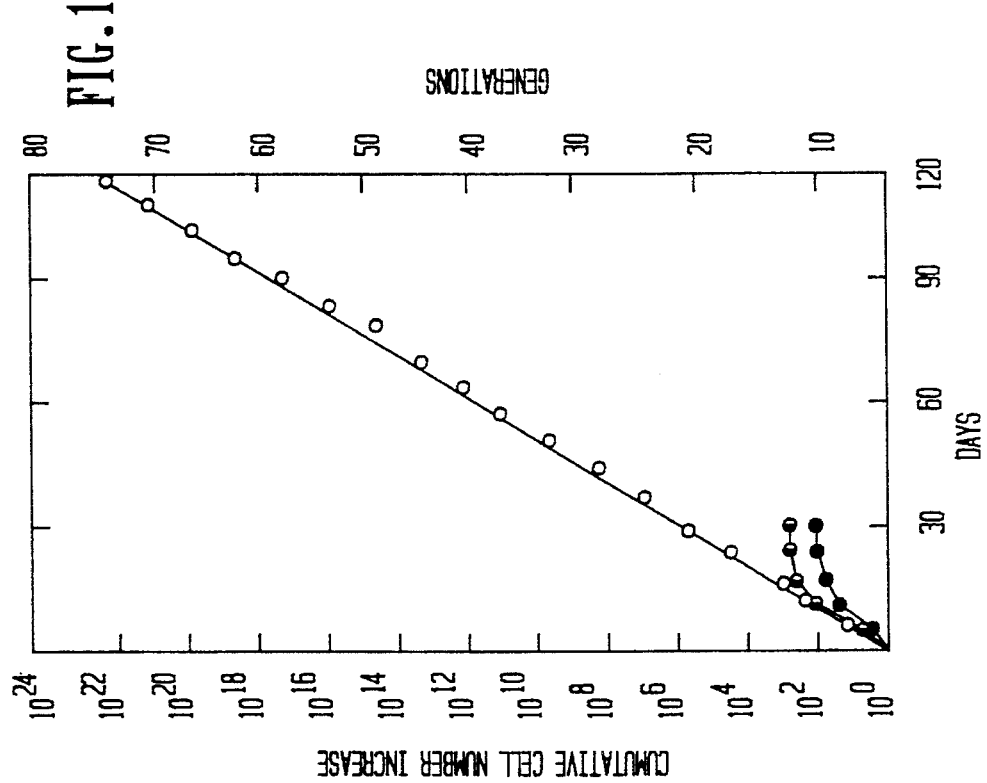
FIG. 1 shows the growth of a representative mouse embryo cell line derived in serum-free medium. ●, culture medium containing 10% calf serum; ○, serum-free culture medium, as described in Example I, infra; ◐, serum-free culture medium containing 10% calf serum.

Mouse embryo cell cultures were derived in serum-free medium from both BALB/c and Swiss embryos. At high cell density, the cells exhibited fibroblastic morphology, with spindle-shaped cells organized into characteristic swirls. Cells maintained in serum-free media grew exponentially without a significant time lag and without crisis (FIG. 1). The number of cells in primary cultures six days after plating was three times higher in serum-free media than in serum-containing media. Cells were split approximately once per week, at a ratio of 1:4 to 1:10. The mouse embryo cells were cultured continually for 200 generations.

Serum-free medium containing the defined supplement of this Example will support the growth of some mouse embryo cell lines established in conventional serum-containing media. In addition, this serum-free medium is related in nutritional and hormonal composition to other media developed for the growth of established lines of mouse embryo cells (Pipas et al., *Cancer Cells* 2:355–363, 1983; Chiang et al., *In Vitro Cell Devel. Biol.* 21:707–712, 1985).

EXAMPLE II

Karyotyping of the Swiss and BALB/c SFME Cell Lines

SFME Swiss and BALB/c cells carried for over 100 generations in serum-free medium were treated with colchicine and karyotyped. The cells were predominately diploid (FIG. 2). No abnormal chromosomes were identified by Giemsa banding. Translocations were detected in some clones derived from the serum-free Swiss cultures, suggesting that cloning or freezing procedures may affect karyotype. One clone containing a translocation was examined further, and found to remain nontumorigenic with a modal chromosome number of 40. Serum-free derived cultures contained a small fraction of cells (4 to 7 percent) with karyotypes in the tetraploid range.

Cell cultures which were grown in serum-containing media, with or without the addition of the described defined supplement, underwent a well-defined crisis, exhibiting abnormal karyotypes and tumorigenic qualities. After several population doublings, 100% of the metaphases of Swiss SFME cells grown in serum-containing medium contained one or more translocated marker chromosomes (FIG. 2). No chromosomal abnormalities were identified in the serum-free derived Swiss and BALB/c SFME cultures.

Chromosome assignments carried out on a number of metaphases revealed that monosomies and trisomies did not involve the same chromosomes, indicating random loss and gain of chromosomes from metaphase to metaphase, rather than a particular chromosomal aberration. This degree of division infidelity was also observed in primary cultures of mouse embryo cells in serum-containing medium that were processed and analyzed in an identical manner. The cells were confirmed to be of mouse origin by isozyme and chromosome analysis, and were free of bacterial and fungal contamination as determined by examination of blood agar and broth cultures inoculated with cells and medium from the cultures.

EXAMPLE III

Examination of the SFME Cell Lines for Tumorigenic Capacity

The tumorigenic capacity of the Swiss SFME line was analyzed by injection of various numbers of cells into athymic mice. Athymic mice were used for these in vivo assays of tumorigenicity because SFME embryo cultures were initiated from outbred mice. The tumorigenic capacity of BALB/c SFME cells was analyzed by injection of cells into syngenic BALB/c mice. The results of in vivo assays are shown in Table 1.

TABLE 1

TUMORIGENIC PROPERTIES OF MOUSE EMBRYO CELL CULTURES

| Cells | Conditions | Results |
| --- | --- | --- |
| BALB/c SFME | BALB/c mouse injection; $10^7$ cells | 0/4 with tumors after 120 days |
| Swiss SFME | Athymic mouse injection; $10^7$ cells | 0/8 with tumors after 240 days |
| KBALB* | Athymic mouse injection; $10^6$ cells | 4/4 with tumors** after 14 days |
| RasSFME*** | Athymic mouse injection; $10^6$ cells | 4/4 with tumors after 14 days |

TABLE 1-continued

TUMORIGENIC PROPERTIES OF MOUSE EMBRYO CELL CULTURES

| Cells | Conditions | Results |
| --- | --- | --- |

*Kirsten sarcoma virus-transformed 3T3 mouse embryo cells
**1 cm diameter tumor
***Human Ha-ras-transformed Swiss SFME cells selected for growth in serum-containing medium The SFME cell lines are non-tumorigenic in athymic mice when injected at cell burdens ten times that necessary for tumor production by virus-transformed cells or by transformed cells expressing an activated ras oncogene. These results suggest that the SFME cell lines may be advantageously used as a host cell for expression of desired biological substances. The SFME Swiss and SFME Balb/C cell lines have been deposited with the American Type Culture Collection under Accession Number CRL 9391, and CRL 9392, respectively.

EXAMPLE IV

Effects of Serum-Free Medium Supplement Components on the Growth of SFME Cells

Examination of the growth response of the SFME line in serum-free medium indicated that the line was extremely sensitive to the omission of insulin or transferrin from the medium. The Swiss SFME cell line showed significant but less marked reduction in growth upon omission of HDL or fibronectin. Cells plated in the absence of fibronectin grow primarily in suspension as clumps unattached to the culture dish. Omission of PDGF produced approximately a 10% reduction in cell number after 6 days in culture, and PDGF was routinely omitted from the serum-free formulation after passage 20. The SFME cells were also found to be absolutely dependent on the presence of EGF in the medium for survival, and died upon its removal from the medium (90% dead within 96 hours) (FIG. 3). The EGF requirement was also observed if MCDB 402, a formulation developed for Swiss 3T3 mouse embryo cells, was used as the basal nutrient medium. Flow cytometric analysis indicated that cells maintained in the absence of EGF accumulated in the G1 phase of the cell cycle prior to loss of viability. Omission of other individual supplement components resulted in decreased cell growth, but did not result in immediate cell death. The addition of the tumor promoter 12-0-tetradecanoylphorbol 13-acetate (TPA) to serum-free medium from which EGF had been omitted extended the life of the culture by several days. Both TPA and transforming growth factor beta greatly improved attachment and spreading of SFME cells.

TABLE 2

EFFECT OF OMISSION OF SUPPLEMENTARY COMPONENTS OF SERUM-FREE MEDIUM FOR SFME CELLS

| Medium | Cell Number |
| --- | --- |
| Complete (all supplements) | $8.6 \times 10^5$ |
| Without HDL | $6.3 \times 10^5$ |
| Without Fibronectin | $4.8 \times 10^5$ |
| Without Insulin | $1.9 \times 10^5$ |
| Without Transferrin | $1.5 \times 10^5$ |
| Without EGF | all dead |

Cells were plated in serum-free medium supplemented as described below and cell number determined four days later by counting cell suspensions in a Coulter particle counter. Cells were plated at $10^5/35$ mm-diameter dish. Swiss SFME cells were used for the experiment. Similar results were obtained with BALB/c SFME cells. Cultures were grown in medium supplemented with 10 ug/ml bovine insulin (Sigma), 25 ug/ml human transferrin (Sigma), 25 ng/ml EGF (Collaborative Research), and 20 ug/ml human ItDL (Meloy) on flasks precoated with 20 ug/ml human fibronectin (Meloy), or in media from which one of the components had been individually omitted. Nutrient medium was a one to one mixture of Dulbecco-modified Eagle's Medium and Ham's F12 (GIBCO) containing 10 nM sodium selenite, 1.2 g/l sodium bicarbonate, 15 mM HEPES buffer, 200 IU/ml penicillin, 200 ug/ml streptomycin and 25 ug/ml ampicillin.

Triiodothyronine, hydrocortisone, and transforming growth factor-beta were inhibitory to the growth of SFME cells in serum-free medium.

Mouse embryo cells derived in serum-free medium were capable of growing to very high densities (FIG. 3). Under these conditions, the cells formed multilayered piles and aggregates. The apparent decrease in growth rate of serum-free mouse embryo cultures at high cell density may be the result of both increased cell loss due to depletion of nutrients and accumulation of cells in G1 due to rapid depletion of EGF. Survival of the cultures at very high cell densities was precarious because of rapid depletion of EGF. The capability for growth while suspended in a low agar concentration, or "anchorage independence" was also investigated. At low cell densities, the SFME lines form colonies in soft agar with low frequency relative to virus-transformed cells, but form colonies with high frequency at high cell densities ($10^{5-6}$ cm plate).

EXAMPLE V

Inhibitory Effects of Serum

Although SFME cells were capable of responding in vitro to a number of physiologically relevant modulators of cell growth, these cells did not grow at an appreciable rate in calf serum- or fetal calf serum-supplemented medium under conditions by which mouse embryo cells derived by conventional protocols could be cultured indefinitely (FIGS. 3 and 4). Both calf serum and platelet-free plasma were effective at inhibiting SFME cell growth; supplementation of serum-containing medium with the growth-stimulatory factors used in the serum-free medium marginally improved cell growth. Inhibition of mouse embryo cell proliferation was reversible upon replacement of serum-containing medium with the serum-free medium. Flow cytometric analysis indicated that cells in serum-containing medium accumulated in the G1 phase of the cell cycle.

The growth inhibitory activity of serum or plasma was partially removed by dialysis or incubation with activated charcoal for 30 minutes at 56° C. Growth inhibition could be observed upon the addition of transforming growth factor beta (10 ng/ml) triiodithyronine (1 nM), thyroxine or other related compounds, hydrocortisone (100 nM), dexamethasone (100 nM) or retinoic acid (1 nM). Inhibitory effects of these compounds were enhanced by the addition of 2–10% charcoal-treated calf plasma. Combinations of these hormones were more effective than individual additions.

EXAMPLE VI

Expression of the Ha-ras Gene in SFME Cells

Swiss and BALB SFME cells were transfected by calcium phosphate precipitation procedures with the moelcularly cloned human Ha-ras oncogene or the ras oncogene together with the mouse cellular myc gene under the control of the SV40 promoter. The transfected SFME cells acquired the ability to grow in serum-free medium from which EGF had been omitted; some clones were capable of growth in serum-containing medium, particularly when supplemented with insulin and EGF. Cells when injected into athymic or syngeneic mice produced undifferentiated sarcomas of undetermined type.

The ability of SFME cells to express exogenously introduced DNA was confirmed by transfection of SFME cells with a plasmid containing a gene conferring resistance to neomycin, followed by isolation of neomycin-resistent cells from the transfected cultures. When the ras oncogene was also present during the transfection at a ten-fold excess over the neomycin-resistance gene, the neomycin-resistant cells were also capable of growth in the absence of EGF.

TABLE 3

GROWTH OF A CLONE OF RAS-TRANSFORMED SWISS SFME

| | Cells per plate (S $10^{-5}$) | | |
|---|---|---|---|
| Day after plating | Serum-free Medium | Medium –EGF | 10% Serum + EGF |
| Day 1 | 1.5 | 1.1 | 1.4 |
| Day 2 | 3.1 | 1.9 | 1.9 |
| Day 3 | 4.2 | 3.3 | 2.3 |
| Day 4 | 7.2 | 5.5 | 3.0 |
| Day 5 | 14 | 12 | 3.6 |
| Day 6 | 23 | 23 | 3.7 |

Cells were plated in serum-free medium as described and cell number determined at 24 hour intervals by counting cell suspensions in a Coulter particle counter. Cells were plated at $10^5/35$ mm-diameter dish. Ras-transformed Swiss SFME cells were used for the experiment. Similar results were obtained with ras-transformed BALB/c SFME cells.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A non-tumorigenic murine cell line which exhibits a predominantly diploid karyotype and is capable of indefinite growth in serum-free media, said cell line being further capable of expressing exogenously introduced genes.

2. The cell line of claim 1 wherein said cell line is derived from mouse embryo cells.

3. The cell line of claim 2 wherein said cell line is derived from embryos from Swiss or BALB/c mice.

4. The cell line of claim 1 wherein said introduced gene is a gene encoding a protein selected from the group consisting of tissue plasminogen activator, factor VIII, interleukin-II, insulin, growth hormone, tumor necrosis factor, superoxide dismutase, and interferon.

5. A non-tumorigenic cell line SFME Swiss (ATCC No. CRL 9391).

6. A non-tumorigenic cell line SFME Balb/C (ATCC No. CRL 9392).

7. A method for selectively controlling the growth of a non-tumorigenic murine cell line which exhibits a predominantly diploid karyotype and is capable of indefinite growth in serum-free media, comprising:

growing said cell line in a serum-free media; and
supplementing said media with a selected amount of a biological substance selected from the group consisting of serum, plasma, conditioned cell culture medium, tissue extracts and purified or partially purified components thereof.

8. The method of claim 7 wherein the serum-free media includes insulin, transferrin, epidermal growth factor, high-density lipoprotein and fibronectin.

9. The method of claim 7, wherein said cell line is selected from the group consisting of SFME Swiss and SFME Balb/C.

* * * * *